United States Patent [19]

Müller et al.

[11] Patent Number: 5,223,517
[45] Date of Patent: Jun. 29, 1993

[54] HETEROCYCLICALLY SUBSTITUTED CYCLOALKANO[B]-INDOLESULPHONA-MIDES

[75] Inventors: Ulrich E. Müller, Wuppertal; Ulrich Niewöhner, Wermelskirchen; Elisabeth Perzborn, Wuppertal; Erwin Bischoff, Wuppertal; Hans-Georg Dellweg, Wuppertal, all of Fed. Rep. of Germany

[73] Assignee: Bayer Aktiengesellschaft, Leverkusen, Fed. Rep. of Germany

[21] Appl. No.: 749,018

[22] Filed: Aug. 23, 1991

[30] Foreign Application Priority Data

Aug. 29, 1990 [DE] Fed. Rep. of Germany ....... 4027278

[51] Int. Cl.⁵ ............ C07D 401/14; C07D 401/12; C07D 401/04; C07D 401/06; C07D 403/14; C07D 403/12; C07D 403/06; C07D 403/04; A61K 31/42; A61K 31/425; A61K 31/415; A61K 31/40; A61K 31/475; A61K 31/50; A61K 31/505; A61K 31/44

[52] U.S. Cl. .................... 514/339; 514/411; 514/381; 514/382; 514/406; 514/256; 514/269; 514/274; 514/307; 514/309; 514/310; 514/311; 514/312; 514/313; 514/314; 514/259; 514/260; 514/249; 514/248; 514/365; 514/369; 514/370; 514/367; 514/372; 514/373; 514/374; 514/376; 514/377; 514/375; 514/378; 514/380; 514/397; 514/394; 514/395; 514/232.8; 514/323; 514/253; 514/254; 544/372; 544/142; 544/237; 544/235; 544/353; 544/354; 544/355; 544/356; 544/284; 544/298; 544/333; 544/322; 544/405; 544/238; 548/439; 548/449; 548/448; 548/450; 548/451; 548/252; 548/253; 548/251; 548/181; 548/159; 548/214; 548/207; 548/212; 548/209; 548/225; 548/235; 548/236; 548/217; 548/221; 548/243; 548/247; 548/364.7; 548/311.4; 548/305.1; 546/200; 546/272; 546/162; 546/161; 546/160; 546/156; 546/154; 546/153; 546/152; 546/168; 546/141; 546/143; 546/146; 546/148

[58] Field of Search .............. 546/272, 200, 161, 154, 546/168, 146; 514/339, 411, 381, 256, 253, 310, 313, 259, 248, 370, 373, 377, 380, 395, 253; 544/372, 235, 355, 298, 405; 548/439, 450, 253, 181, 207, 225, 217, 247

[56] References Cited

U.S. PATENT DOCUMENTS

4,988,820  1/1991  Boshagen et al. .................. 548/439

FOREIGN PATENT DOCUMENTS

0269452  6/1988  European Pat. Off. .
0300675  1/1989  European Pat. Off. .
3631824  3/1988  Fed. Rep. of Germany .

OTHER PUBLICATIONS

Okawa et al., Chemical Abstracts vol. 69, Entry 37117u (1968).
Hahn et al., Chemical Abstracts, vol. 85, entry 94224f (1976).
Boeshagen et al., Chemical Abstracts, vol. 109, entry 230800j (1988).

Primary Examiner—John M. Ford
Attorney, Agent, or Firm—Sprung Horn Kramer & Woods

[57] ABSTRACT

Heterocyclically substituted cycloalkano[b]-indolesulphonamides can be prepared by reaction of appropriate N-unsubstituted indoles with acrylonitrile, followed by hydrolysis, esterification or amidation, or by reaction of heterocyclically substituted hydrazines with cycloalkanones or by subsequent introduction of the heterocyclic group into appropriate indole derivatives. The heterocyclically substituted cycloalkano[b]-indolesulphonamides can be employed for the treatment of thromboembolic disorders, ischaemias, arteriosclerosis, asthma, allergies and for the prophylaxis of myocardial infarcts.

10 Claims, No Drawings

HETEROCYCLICALLY SUBSTITUTED CYCLOALKANO[B]-INDOLESULPHONAMIDES

The invention relates to heterocyclically substituted cycloalkano[b]-indolesulphonamides, to processes for their preparation and to their use in medicaments.

It has already been disclosed that cycloalkano[b-]dihydroindole- and -indolesulphonamides have a platelet aggregation-inhibiting action [cf. German Offenlegungsschrift 3,631,824].

Heterocyclically substituted cycloalkano[b]-indolesulphonamides of the general formula (I)

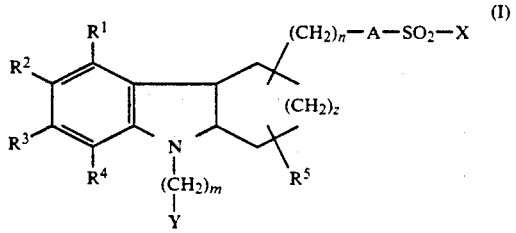

in which
$R^1$, $R^2$, $R^3$, $R^4$ and $R^5$ are identical or different and
represent hydrogen, nitro, cyano, halogen, trifluoromethyl, carboxyl, hydroxyl or trifluoromethoxy, or
represent a group of the formula $-S(O)_w R^6$, in which
$R^6$—denotes straight-chain or branched alkyl having up to 8 carbon atoms or aryl having 6 to 10 carbon atoms, which, for its part, is substituted by halogen, nitro, cyano or trifluoromethyl
and
w—denotes a number 0, 1 or 2,
or
represent straight-chain or branched alkoxy or alkoxycarbonyl in each case having up to 10 carbon atoms or benzyloxy, or
represent a group of the formula $-NR^7R^8$,
in which
$R^7$ and $R^8$ are identical or different and
denote hydrogen, straight-chain or branched alkyl or acyl in each case having up to 8 carbon atoms or
denote aryl having 6 to 10 carbon atoms,
or
represent cycloalkyl having 3 to 8 carbon atoms or
represent aryl having 6 to 10 carbon atoms, or
represent straight-chain or branched alkyl or alkenyl in each case having up to 10 carbon atoms, which are optionally substituted by halogen, hydroxyl, carboxyl, cyano, aryl having 6 to 10 carbon atoms, straight-chain or branched alkyl, alkoxy or alkoxycarbonyl in each case having up to 8 carbon atoms or by a group of the formula

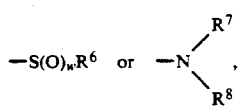

in which
w, $R^6$, $R^7$ and $R^8$ have the abovementioned meaning, or
represent a group of the formula —D, —E—O—L—D, —E—NH—L—D,
—E—CO—L—D or —E—D, in which
D—denotes a 3- to 7-membered, saturated or unsaturated heterocycle having up to 4 heteroatoms from the series comprising N, O or S, to which further aromatic or heterocyclic rings can be fused,
and
E and L are identical or different and
denote a direct bond or
denote straight-chain or branched alkylene or alkenylene having up to 10 carbon atoms,
X—represents aryl having 6 to 10 carbon atoms, which is optionally monosubstituted to pentasubstituted by identical or different substituents from the series comprising nitro, halogen, cyano, trifluoromethyl, trifluoromethoxy, trifluoromethylthio, hydroxyl, carboxyl, aryl or aryloxy having 6 to 10 carbon atoms and straight-chain or branched alkoxy or alkoxycarbonyl in each case having up to 8 carbon atoms or by straight-chain or branched alkyl having up to 8 carbon atoms, it being possible for the alkyl, for its part, to be substituted by carboxyl, hydroxyl, alkoxycarbonyl having up to 6 carbon atoms, by aryl having 6 to 10 carbon atoms, or by a group of the formula $-S(O)_w R^6$ or $-NR^7R^8$,
in which
w, $R^6$, $R^7$ and $R^8$ have the abovementioned meaning,
or
represents straight-chain or branched alkyl having up to 8 carbon atoms or
represents trifluoromethyl,
m—represents the number 1, 2, 3 or 4,
n—represents the number 0, 1 or 2,
z—represents a number 1, 2, 3 or 4,
A—represents a direct bond or a group of the formula $$-NH- \text{ or } -\underset{|}{N}-E-D,$$

in which
D and E have the abovementioned meaning,
Y—represents the group of the formula —CO—G,
in which
G—denotes hydroxyl, alkoxy having up to 8 carbon atoms, phenoxy or a group of the formula $-NR^7R^8$ or $-NH-SO_2-R^6$,
in which
$R^6$, $R^7$ and $R^8$ have the abovementioned meaning, or
represents tetrazolyl,
with the proviso that either the substituent A must represent the radical —N—E—D or at least one of the substituents $R^1$, $R^2$, $R^3$, $R^4$ and $R^5$ must represent one of the groups —D, —E—O—L—D, —E—NH—L—D, —E—CO—L—D or —E—D, if appropriate in an isomeric form, and their salts, have now been found.

The heterocyclically substituted indolesulphonamides according to the invention have one or more asymmetric carbon atoms and can therefore exist in various stereochemical forms.

The compounds exist in stereoisomeric forms which behave either as image and mirror image (enantiomers) or which do not behave as image and mirror image (diastereomers). The invention relates both to the antipodes and to the racemic forms and the diastereomeric mixtures. The racemic forms, like the diastereomers, can be separated into the stereoisomerically homogeneous constituents in a known manner (cf. E. L. Eliel, Stereochemistry of Carbon Compounds, McGraw Hill, 1962).

Regioisomers can additionally occur. The invention relates to both the individual isomers and their mixtures.

Isomeric forms of the heterocyclically substituted indolesulphonamides are listed by way of example below:

a) Cycloalkano[b]indolesulphonamides

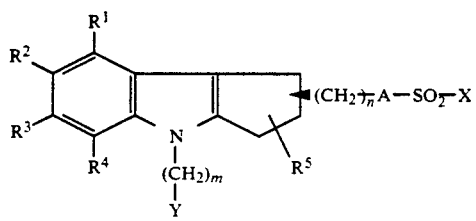

(II)

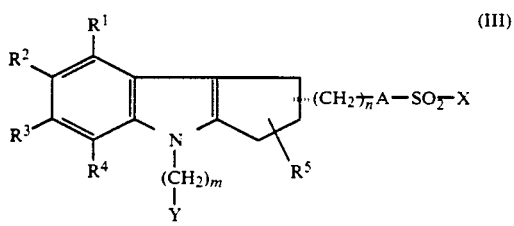

(III)

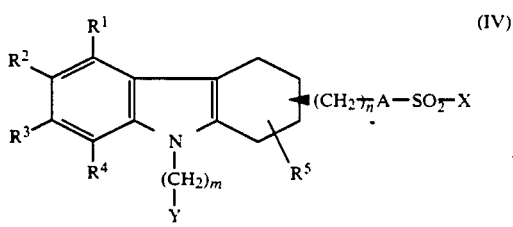

(IV)

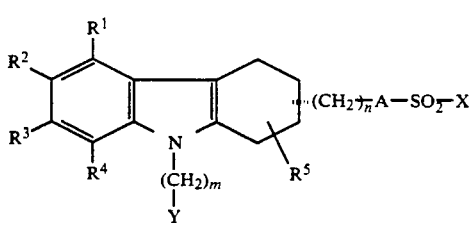

(V)

b) Cycloalkano[b]dihydro-indolesulphonamides

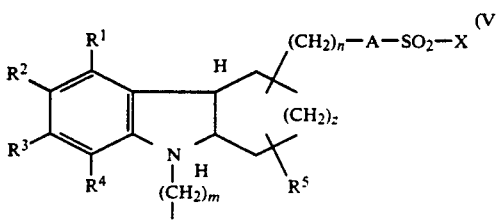

(VI)

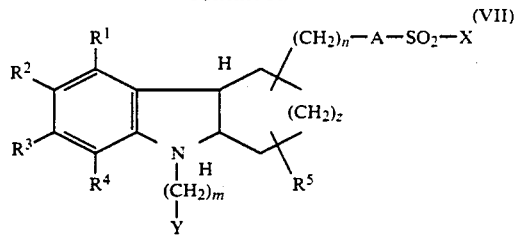

(VII)

where $R^1$, $R^2$, $R^3$, $R^4$, $R^5$, A, X, Y, m, n and z have the abovementioned meaning.

The heterocyclically substituted cycloalkano[b]-indolesulphonamides according to the invention can also be present in the form of their salts. In general, salts with organic or inorganic bases or acids may be mentioned here.

In the context of the present invention, physiologically acceptable salts are preferred. Physiologically acceptable salts of the heterocyclically substituted cycloalkano[b]-indolesulphonamides can be metal or ammonium salts of the substances according to the invention which have a free carboxyl group. Particularly preferred salts are, for example, sodium, potassium, magnesium or calcium salts, and ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts are those with inorganic acid such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

Heterocycle in general represent a 5- to 7-membered, preferably 5- to 6- membered, saturated or unsaturated ring, which, as heteroatoms, can contain up to two oxygen, sulphur and/or nitrogen atoms and to which further aromatic or heterocyclic rings can be fused. 5- and 6-membered rings containing an oxygen, sulphur and/or up to two nitrogen atoms, which can also be benzo-fused, are preferred.

The following are mentioned as preferred: thienyl, furyl, pyrrolyl, pyrazolyl, pyridyl, pyrimidyl, pyrazinyl, pyridazinyl, quinolyl, isoquinolyl, quinazolyl, quinoxazolyl, cinnolyl, thiazolyl, benzothiazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl, piperazinyl.

The substances according to the invention surprisingly have a platelet aggregation-inhibiting action, additionally cause an inhibition of thromboxane synthase in isolated platelets and can be used for the therapeutic treatment of humans and animals.

Preferred compounds of the general formula (I) are those
in which
$R^1$, $R^2$, $R^3$, $R^4$ and $R^5$ are identical or different and represent hydrogen, fluorine, chlorine, bromine, nitro, cyano, trifluoromethyl, carboxyl, hydroxyl or trifluoromethoxy, represent a group of the formula $-S(O)_wR^6$, in which $R^6$—denotes straight-chain or branched alkyl having up to 6 carbon atoms or phenyl, which, for its part, can be substituted by fluorine, chlorine, bromine, nitro, cyano or trifluoromethyl, w—denotes a number 0, 1 or 2, or represent straight-chain or branched alkoxy or alkoxycarbonyl in each case having up to 8 carbon atoms, or represent a group of the formula $-NR^7R^8$, in which $R^7$ and $R^8$ are identical or different and denote hydrogen, straight-chain or branched alkyl having up to 6 carbon atoms or phenyl, or represent cyclopropyl, cyclopentyl, cyclohexyl or phenyl, or represent straight-chain or branched alkyl or alkenyl in each case having up to 8 carbon atoms, which are optionally substituted by fluorine, chlorine, bromine, hydroxyl, carboxyl, cyano, phenyl, straight-chain or branched alkyl, alkoxy or alkoxycarbonyl in each case having up to 6 carbon atoms or by a group of the formula $-S(O)_wR^6$ or $-NR^7R^8$, in which w, $R^6$, $R^7$ and $R^8$ have the abovementioned meaning, or represent a radical or a group of the formula —D, —E—O—L—D, —E—NH—L—D, —E—CO—L—D or —E—D, in which D—denotes pyridyl, quinolyl, tetrazolyl, benzothiazolyl, isoquinolyl, benzimidazolyl, pyrimidyl, pyrrolyl, thienyl, furyl, imidazolyl or thiazolyl, and E and L are identical or different and denote a direct bond or denote straight-chain or branched alkyl or alkenyl in each case having up to 8 carbon atoms, X represents phenyl which is optionally monosubstituted to tetrasubstituted by identical or different substituents from the series comprising nitro, hydroxyl, fluorine, chlorine, bromine, iodine, cyano, trifluoromethyl, trifluoromethoxy, hydroxyl, carboxyl, phenyl, phenoxy and straight-chain or branched alkoxy or alkoxycarbonyl in each case having up to 6 carbon atoms or by straight-chain or branched alkyl having up to 6 carbon atoms, or represents straight-chain or branched alkyl having up to 6 carbon atoms or trifluoromethyl, m—represents the number 1, 2 or 3, n—represent the number 0 or 1, z—represents a number 1, 2 or 3, A—represents a direct bond or a group of the formula $$-\underset{|}{\text{N}}\text{H} \quad \text{or} \quad -\underset{|}{\text{N}}-\text{E}-\text{D}$$

in which

D and E have the abovementioned meaning,

Y—represents the group of the formula —CO—G, in which

G—denotes hydroxyl, alkoxy having up to 6 carbon atoms, phenoxy or the group $-NHSO_2R^6$, in which $R^6$ has the abovementioned meaning, or represents tetrazolyl, with the proviso that either the substituent A must represent the radical —N—E—D or at least one of the substituents $R^1$, $R^2$, $R^3$, $R^4$ and $R^5$ must represent one of the groups —D, —E—O—L—D, —E—NH—L—D, —E—CO—L—D or —E—D, if appropriate in an isomeric form, and their salts.

Particularly preferred compounds of the general formula (I) are those in which $R^1$, $R^2$, $R^3$, $R^4$ and $R^5$ are identical or different and represent hydrogen, fluorine or chlorine, represent a group of the formula $-S(O)_w-R^6$, in which $R^6$—denotes straight-chain or branched alkyl having up to 4 carbon atoms or phenyl, which, for its part, can be substituted by fluorine, chlorine or bromine and w—denotes the number 2, or represent straight-chain or branched alkoxy or alkoxycarbonyl in each case having up to 4 carbon atoms, or represent the group of the formula $-NR^7R^8$, in which $R^7$ and $R^8$ are identical or different and denote hydrogen, straight-chain or branched alkyl having up to 4 carbon atoms or phenyl, or represent straight-chain or branched alkyl having up to 6 carbon atoms which are optionally substituted by fluorine, chlorine, bromine, hydroxyl, cyano or phenyl, or represent a radical or a group of the formula —D, —E—O—L—D, —E—CO—L—D or —E—D, in which D—denotes pyridyl, pyrimidyl, imidazolyl or thiazolyl, and E and L are identical or different and denote a direct bond or denote straight-chain or branched alkyl having up to 6 carbon atoms, X—represents phenyl which is optionally monosubstituted to trisubstituted by identical or different substituents from the series comprising fluorine, chlorine, bromine, cyano, trifluoromethyl and trifluoromethoxy or by straight-chain or branched alkyl, alkoxy or alkoxycarbonyl in each case having up to 4 carbon atoms, m—represents the number 1 or 2, n—represents the number 0 or 1, z—represents a number 1 or 2, A—represents a direct bond or a group of the formula

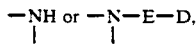

in which

D and E have the abovementioned meaning,

Y—represents the group of the formula —CO—G, in which

G—denotes hydroxyl, alkoxy having up to 4 carbon atoms or the group —NHSO$_2$R$^6$, in which R$^6$ has the abovementioned meaning, or represents tetrazolyl, with the proviso that either the substituent A must represent the radical

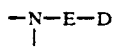

or at least one of the substituents R$^1$, R$^2$, R$^3$, R$^4$ and R$^5$ must represent one of the groups —D, —E—O—L—D, —E—NH—L—D, —E—CO—L—D or —E—D, if appropriate in an isomeric form, and their salts.

The compounds of the general formula (I) can be prepared by a process in which

[A] in the case in which m represents the number 2, compounds of the general formula (VIII)

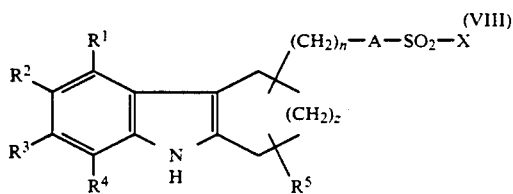

in which

R$^1$, R$^2$, R$^3$, R$^4$, R$^5$, z, n, A and X have the abovementioned meaning, are reacted with acrylonitrile, if appropriate in the presence of a base, in inert solvents to give compounds of the general formula (IX)

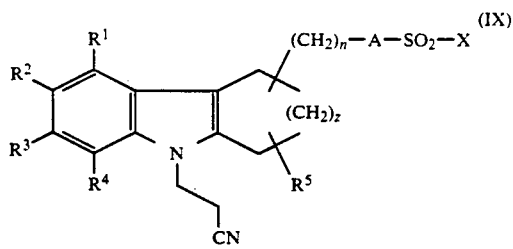

in which

R$^1$, R$^2$, R$^3$, R$^4$, R$^5$, z, n, A and X have the abovementioned meaning, in the case in which Y represents the tetrazole ring, these are reacted with sodium azide in the presence of triethylamine hydrochloride, or in the case of the preparation of the acids (Y=COOH), the cyano group is hydrolysed by a customary method, in the case of the preparation of the esters (Y=C$_1$-C$_8$-alkoxycarbonyl, phenoxycarbonyl), the acids are reacted by a customary method with the appropriate alcohols in the presence of a catalyst, if appropriate in inert solvents, in the case of the preparation of the amides and acylsulphonamides (Y=—CONR$^7$R$^8$, —CO—NH—SO$_2$—R$^6$), either the esters or the acids are reacted, after customary activation, with the amines or sulphonamides of the general formulae (Xa) and (Xb)

in which

R$^6$, R$^7$ and R$^8$ have the abovementioned meaning, if appropriate in the presence of a catalyst, or by a process in which

[B] compounds of the general formula (XI)

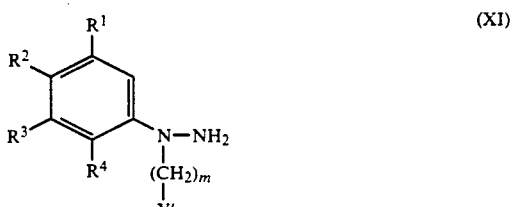

in which

R$^1$, R$^2$, R$^3$, R$^4$, and m have the abovementioned meaning, and

Y'—represents (C$_1$-C$_4$)-alkoxycarbonyl or cyano, are reacted with cycloalkanesulphonamides of the general formula (XII)

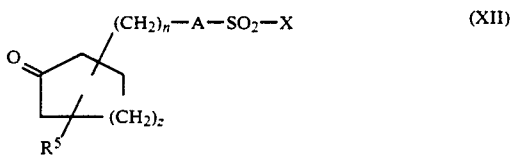

in which z, n, A, R$^5$ and X have the abovementioned meaning, in inert solvents, if appropriate in the presence of a catalyst, in the case of the preparation of the acids (Y=COOH), the esters or cyano group are hydrolysed by a customary method, in the case of the preparation of esters (Y=C$_1$-C$_8$-alkoxycarbonyl, phenoxycarbonyl), the acids are reacted by a customary method with the appropriate alcohols in the presence of a catalyst, if appropriate in inert solvents, or esters are transesterified by customary methods, in the case of the preparation of the amides and sulphonamides (Y=—CONR$^7$R$^8$, —CO—NHSO$_2$—R$^6$), either the esters are reacted directly, or the acids are reacted after customary activation, with the amines or sulphonamides of the general formulae (Xa) and (Xb) if appropriate in the presence of a catalyst, in the case in which Y represents the tetrazole ring, the cyano compound (Y=CN) is reacted with sodium azide in the presence of triethylamine hydrochloride, or by a process in which

[C] the radicals of the formula —D, —E—O—L—D, —E—NH—L—D, —E—CO—L—D or —E—D are introduced by customary methods, for example by nucleophilic or electrophilic aromatic substitution into compounds of the general formula (Ia)

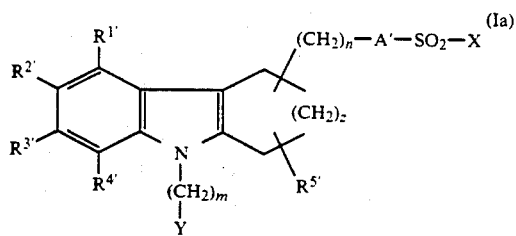

in which

R$^{1'}$, R$^{2'}$, R$^{3'}$, R$^{4'}$ and R$^{5'}$ have the meaning indicated, but do not represent a group of the formula —D, —E—O—L—D, —E—NH—L—D, —E—CO—L—D or —ED, A' represents the group —NH— and m, Y, X and z have the meaning indicated, the radicals of the formula —D, —E—O—L—D, —E—NH—L—D, —E—CO—L—D or —E—D are introduced by customary methods, for example by nucleophilic or electrophilic aromatic substitution and, if appropriate, carbonyl groups are reduced to methylene groups by customary methods, in the case of the preparation of the acids (Y=—COOH), the esters are hydrolysed by a customary method, in the case of the variation of the esters (Y=C$_1$-C$_8$-alkoxycarbonyl, phenoxycarbonyl), the acids are reacted by a customary method with the appropriate alcohols in the presence of a catalyst, if appropriate in inert solvents, in the case of the amides and acylsulphonamides (Y=—CONR$^7$R$^8$, —CO—NHSO$_2$—R$^6$), either the esters are reacted directly, or the acids are reacted after customary activation, with the amines or sulphonamides of the general formulae (Xa) and (Xb), if appropriate in the presence of a catalyst, and then in the case of the heterocyclically substituted cycloalkano[b]-dihydroindolesulphonamides, the heterocyclically substituted indolesulphonamides prepared by process [A], [B] or [C] are reduced in inert solvents in the presence of a reducing agent, if appropriate the isomers are separated and in the case of the preparation of the salts reacted with an appropriate base or acid.

The process according to the invention can be illustrated by way of example by the following reaction scheme:

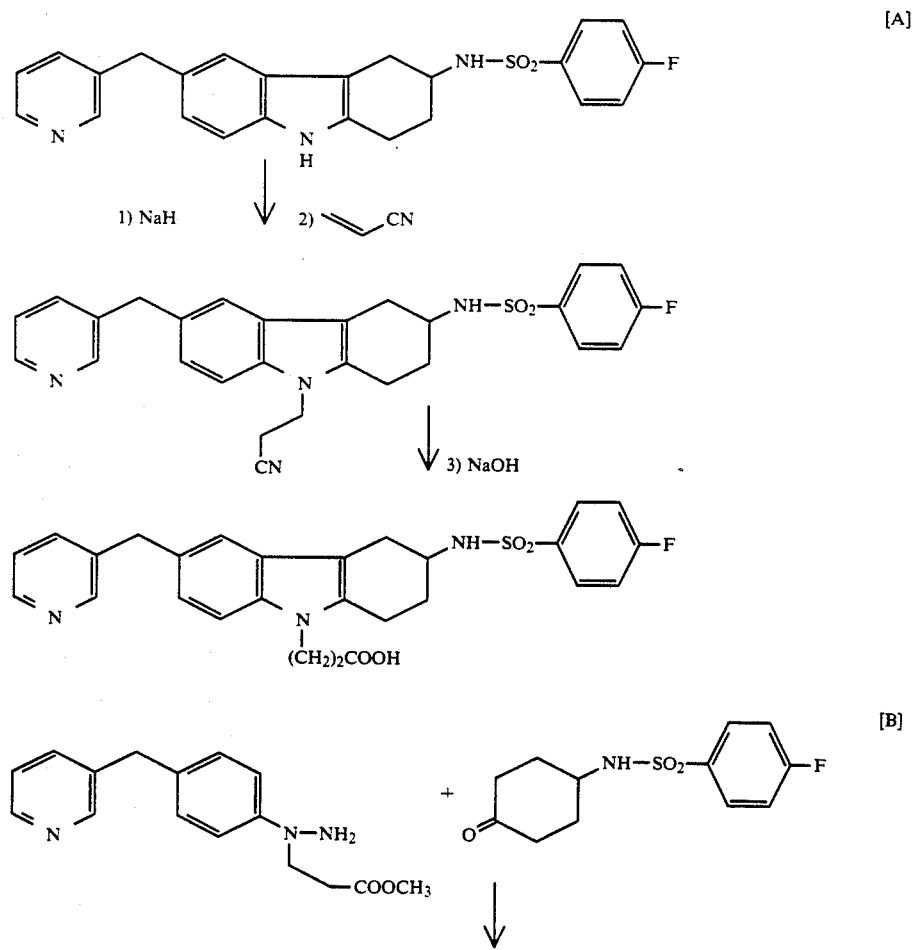

-continued
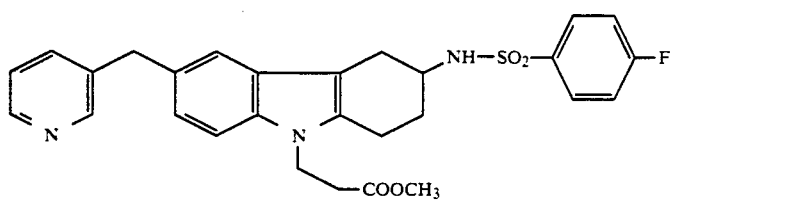
[C]
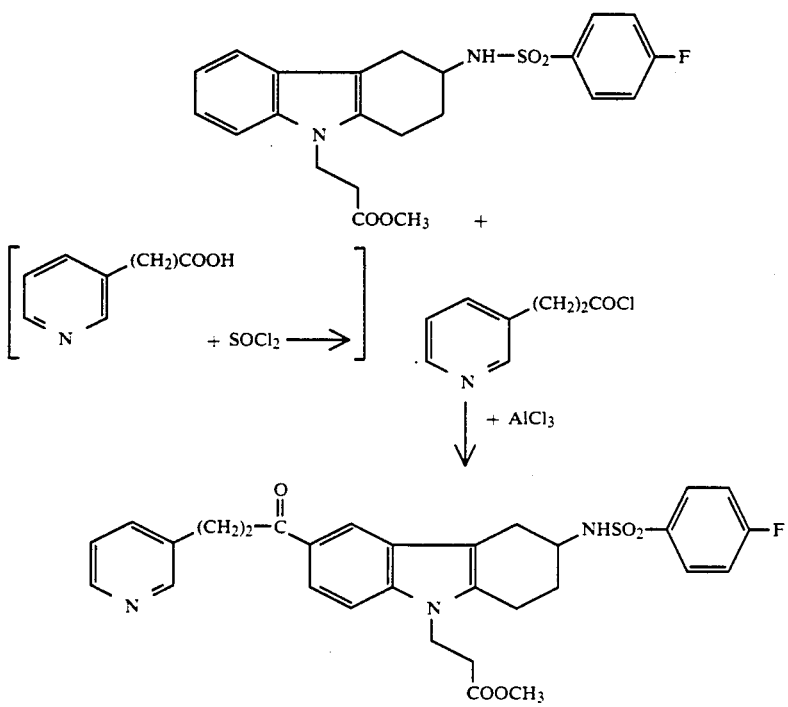
a) NaOH  b) 1) NaBH₄  c) NH₃
              2) NaOH
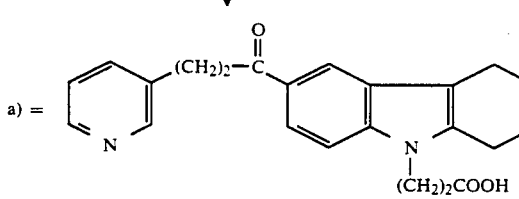
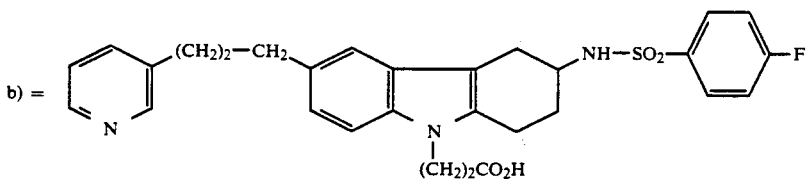
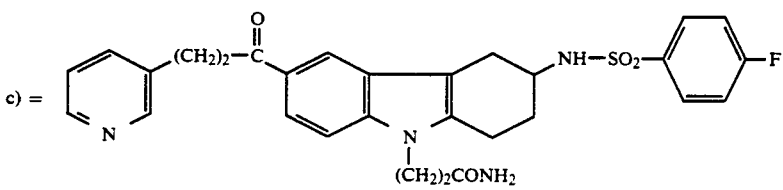
Solvents for processes [A] and [B] according to the invention can be water and organic solvents which do not change under the reaction conditions. These preferably include chlorinated hydrocarbons, such as, for example, chloroform or methylene chloride, alcohols such as methanol, ethanol, propanol or isopropanol, ethers such as diethyl ether, tetrahydrofuran, dioxane, glycol monomethyl ether or glycol dimethyl ether, hydrocarbons such as benzene, toluene, xylene, cyclohexane, hexane or mineral oil fractions, dimethyl sulphoxide, dimethylformamide, hexamethylphosphoric triamide, ethyl acetate, acetonitrile or pyridine. It is also possible to use mixtures of the solvents mentioned.

Bases for processes [A] and [B] according to the invention can be customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate, potassium carbonate, or alkali metal alkoxides such as, for example, sodium methoxide or ethoxide, potassium methoxide or ethoxide or potassium tert.-butoxide or amides such as sodium amide or lithium diisopropylamide, or organic amines or ammonium salts such as benzyltrimethylammonium hydroxide, tetrabutylammonium hydroxide, pyridine, triethylamine or N-methylpiperidine.

The processes [A] and [B] according to the invention are in general carried out in a temperature range from 0° C. to 150° C., preferably from 0° C. to 100° C.

In general, processes [A] and [B] are carried out at normal pressure. However, it is also possible to work at reduced pressure or at elevated pressure (for example from 0.5 to 5 bar).

Hydrolysis of the esters is carried out by a customary method, by treating the esters in inert solvents with customary bases, it being possible to convert the initially formed salts into the free carboxylic acids by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferred. It is also possible to employ mixtures of the solvents mentioned.

The hydrolysis is in general carried out in a temperature range from 0° C. to +140° C., preferably from +20° C. to +100° C.

The hydrolysis is in general carried out at normal pressure. However, it is also possible to work at reduced pressure or at elevated pressure (for example from 0.5 to 5 bar).

When carrying out the hydrolysis, the base is in general employed in an amount from 1 to 5 mol, preferably from 1 to 2 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include mineral acids such as, for example, hydrochloric acid, hydrobromic acid, sulphuric acid or phosphoric acid. It has proved advantageous in the preparation of the carboxylic acids in this case to acidify the basic reaction mixture from the hydrolysis in a second step without isolation of the carboxylates. The acids can then be isolated in a customary manner. In the case of the basic heterocycles, the salts of these heterocycles with the inorganic acids can also be obtained by treating the solutions of the carboxylates with the abovementioned acids.

The acids are esterified by a customary method, by reacting the acids in the presence of a catalyst, if appropriate in one of the abovementioned solvents, with the appropriate alcohols. Preferably, this alcohol is also employed as a solvent.

Catalysts which can be employed are inorganic acids, such as, for example, sulphuric acid or inorganic acid chlorides, such as, for example, thionyl chloride.

In general, 0.01 to 1, preferably 0.05 to 0.5, mol of catalyst are employed relative to 1 mol of reactant.

The amidation is carried out in one of the abovementioned solvents, preferably in alcohols such as ethanol or methanol, in a temperature range of 0° C. to +50° C., preferably from +10° to +30° C., and at normal pressure.

Both the esterification and the amidation can proceed, if appropriate, via the acid halide activated stage (I, Y=CO-halogen), which can be prepared from the corresponding acid by reaction with thionyl chloride, phosphorus trichloride, phosphorus pentachloride, phosphorus tribromide or oxalyl chloride.

Suitable Lewis acids are BF$_3$, aluminium halides, such as AlCl$_3$, ZnCl$_2$ or Ag$^\oplus$ salts. BF$_3$ and AlCl$_3$ are preferred.

The compounds of the general formula (VIII) are new and can be prepared by a process in which substituted anilines of the general formula (XIII)

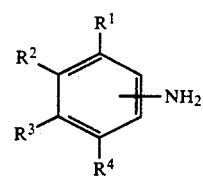

(XIII)

in which

R$^1$, R$^2$, R$^3$ and R$^4$ have the abovementioned meaning, are converted in a two-step reaction, initially with sodium nitrite in the presence of acids and subsequently with sodium bisulphite, into the corresponding hydrazines of the general formula (XIV)

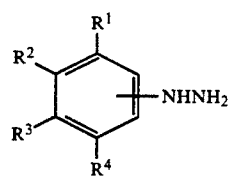

(XIV)

in which

R$^1$, R$^2$, R$^3$ and R$^4$ have the abovementioned meaning, and then reacted with cycloalkanonesulphonamides of the general formula (XII)

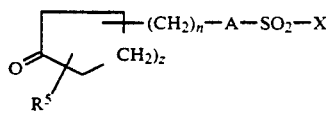

in which

R[5], z, n, A and Z have the abovementioned meaning,
in the presence of the abovementioned inert solvents, if appropriate in the presence of a catalyst.

The compounds of the general formula (IX) are also new and can be prepared as indicated above.

The reaction with phenylhydrazines of the formula (XIV) proceeds under the reaction conditions described for process [B].

Suitable acids for the preparation of hydrazine (1st step) are inorganic acids or their salts, such as, for example, hydrochloric acid or sulphuric acid.

The substituted anilines of the general formula (XIII) are known per se or can be prepared via the respective nitro compound step by reduction methods known from the literature, for example using hydrogen on Pd/C [cf. EP 69,521; J. Med. Chem. 19, 1079 (1976); J. Heterocycl. Chem. 21, 1849, (1984)].

The hydrazines of the general formula (XIV) are known in some cases and can be prepared, however, by the abovementioned method.

The cycloalkanonesulphonamides of the general formula (XII) are known in some cases (R[5]=H) or are new and can be prepared in this case in analogy to the process published in German Offenlegungsschrift 3,631,824 with additional introduction of the substituent (R[5]≠H) by a customary method.

The enantiomerically pure compounds of the general formula (I) according to the invention can be obtained by customary methods, for example in analogy to the process described in German Offenlegungsschrift 3,631,824.

The compounds of the general formula (XI) are known in some cases or can be prepared in analogy to methods known from the literature [cf., for example, German Offenlegungsschrift 2,312,256].

The amines of the general formula (Xa) are known in some cases [cf. Houben-Weyl, "Methoden der organischen Chemie" (Methods of Organic Chemistry), Vol. XI/1 and XI/2].

The sulphonamides of the general formula (Xb) are known in some cases [cf. Beilstein, 11, 26].

The heterocyclically substituted cycloalkano[b]-indolesulphonamides and their salts and isomers can be employed as active compounds in medicaments. The substances have a platelet aggregation-inhibiting and thromboxane A2-antagonist action and inhibit the thromboxane synthase in isolated platelets. They can be employed for the treatment of thromboembolic disorders and ischaemias such as myocardial infarct, stroke, transitory and ischaemic attacks, angina pectoris, peripheral circulatory disorders, prevention of restenoses such as after thrombolysis therapy, percutaneous transluminal angioplasties (PTA), percutaneous transluminal coronary angioplasties (PTCA), by-pass and for the treatment of arteriosclerosis, asthma and allergies.

Blood from healthy subjects of both sexes was used for the determination of the platelet aggregation-inhibiting action. As an anticoagulant, one part of 3.8% strength aqueous sodium citrate solution was admixed to 9 parts of blood. Platelet-rich citrate plasma (PRP)[1] is obtained from this blood by means of centrifugation (Jürgens/Beller, Klinische Methoden der Blutgerinnungsanalyse (Clinical Methods of Blood Coagulation Analysis); Thieme Verlag, Stuttgart, 1959).

For these investigations, 0.8 ml of PRP and 0.1 ml of the active compound solution were preincubated in a water bath at 37° C. The platelet aggregation was then determined by the turbidometric method (Born, G. V. R., J. Physiol. (London), 162, 67, 1962) in an aggregometer at 37° C. (Therapeutische Berichte 47, 80–86, 1975). To this end, 0.1 ml of collagen, an aggregation-inducing agent, was added to the preincubated sample. The change in the optical density in the sample of PRP[1] was recorded during a period of 6 minutes and the results was determined after 6 minutes. To do this, the percentage inhibition is calculated compared to the control.

The range of the minimum effective concentration is given as the threshold concentration.

| Example No. | TAI threshold concentration (μg/ml) |
|---|---|
| 17 | 0.03–0.1 |
| 18 | 0.3–1 |
| 20 | 0.03–0.1 |
| 25 | 0.03–0.1 |

Measurement of the thromboxane synthase in washed human platelets

1. Preparation of platelet suspensions

Blood from healthy donors is taken up in EDTA (1% in 0.9% NaCl, 9+1) and centrifuged at 1000 rpm (150 g) for 20 min. The platelet-rich plasma (PRP)[2] is taken off and in each case 10 ml are centrifuged at 2500 rpm for 20 min. The platelet-rich plasma[2] is decanted off. The platelets which remain are suspended in 5 ml of resuspension buffer (0.15M TRIS/0.9% NaCl/77 mmol EDTA, 8:91:1; adjusted to pH 7.4 with 1N HCl), centrifuged for 20 min at 2500 rpm and suspended in 1 ml of resuspension buffer. The platelet count is adjusted to $3 \times 10^5/\mu l$.

2. Measurement of the thromboxane synthase 1 ml of the platelet suspension and 0.01 ml of the test preparation in 10% DMSO are incubated at 37° C. for 2 min. 0.1 ml of $^3$H-arachidonic acid from Amersham Buchler GmbH and Co. KG ($6.6 \times 10^{-5}$ mol/l) having a specific activity of 140 MBq/mmol are added to this and the mixture is incubated at 37° C. for a further 10 min. After the reaction, the mixture is acidified using about 0.02 ml of 0.5N citric acid and immediately extracted 3 times with 1 ml of ethyl acetate each time. The supernatants are collected in 10 ml glass tubes and the ethyl acetate is blown off at 25° C. under $N_2$. The residue is taken up in 50 μl of MeOH/CHCl$_3$ (1:1) and applied to TLC glass plates (silica gel 60, F254, 20×20 cm, Merck). Separation is carried out in an eluent mixture of CHCl$_3$/MeOH/glacial acetic acid/H$_2$O (80:8:1:0.8). The distribution of the radioactivity is detected in a Ramona-Ls TLC scanner from Raytest and quantitatively evaluated using an integration program.

The concentration of the test substance which leads to a 50% inhibition of thromboxane formation compared to the control is determined.

| Example No. | IC$_{50}$ mol/l |
|---|---|
| 11 | $2 \times 10^{-7}$ |

| Example No. | IC$_{50}$ mol/l |
|---|---|
| 17 | 1 × 10$^{-6}$ |
| 24 | 1 × 10$^{-7}$ |

Thromboxane receptor binding test on human platelet membranes a) Membrane preparation The blood taken the previous evening according to standard methods was centrifuged in the morning at 2800 rpm for 10 min at 10° C. 10 μM indomethacin was added to the buffy coat formed during the course of this as a layer between the platelet-poor plasma and the erythrocytes. Platelet membranes were prepared from the buffy coat by a method which was described by Barber and Jamieson (cf. Barber, A. J., Jamieson, G. A.: Isolation and characterization of plasma membranes from human blood platelets, J. Biol. Chem. 245, 6357–6365, 1970). As the most important step here, platelets are loaded with glycerol and lysed by osmotic shock.

The washed membranes obtained in this way were resuspended in tris-NaCl-glucose buffer (50 mM tris, 100 mM NaCl, 5 mM glucose, pH 7.4), rapidly frozen in dry ice and stored at −70° C.

b) Displacement studies

For the displacement studies, 100 μg of membrane protein and about 5 nM $^3$H-(3R)-3-(4-fluorophenylsulphonamido)-9-(2-carboxyethyl)-1,2,3,4-tetrahydrocarbazole [for preparation cf. German Offenlegungsschrift 3,631,824; radioactive labelling is carried out by a method known from the literature] were incubated in a total volume of 1 ml of tris-NaCl-glucose buffer. Increasing concentrations of the displacing unlabelled compounds according to the invention dissolved in DMSO were added to the mixture (final concentration, 0.5% DMSO, relative to the assay volume).

The substance concentration IC$_{50}$ which is needed to displace 50% of the specific binding was determined with the aid of a logit-log plot according to HILL. The inhibition constant K$_I$ was determined from the IC$_{50}$ and the dissociation constants K$_D$ (determined by Scatchard analysis).

The present invention also includes pharmaceutical preparations which contain one or more compounds of the general formula (I) in addition to inert, non-toxic, pharmaceutically suitable auxiliaries and excipients, or which consist of one or more active compounds of the formula (I), and processes for the production of these preparations.

The active compounds of the formula (I) should be present in these preparation in a concentration of 0.1 to 99.5% by weight, preferably of 0.5 to 95% by weight of the total mixture.

In addition to the active compounds of the formula (I), the pharmaceutical preparations may also contain other pharmaceutical active compounds.

The abovementioned pharmaceutical preparations can be prepared in a customary manner according to known methods, for example with the auxiliary, auxiliaries or excipient(s).

In general, it has proved advantageous to administer the active compound(s) of the formula (I) in total amounts from about 0.03 to about 30 mg/kg, preferably up to about 5 mg/kg of body weight every 24 hours, if appropriate in the form of several individual doses, to achieve the desired result.

An individual dose contains the active compound(s) preferably in amounts from 0.01 to about 10, particularly preferably 0.1 to 1.0, mg/kg of body weight.

If appropriate, however, it may be advantageous to depart from the amounts mentioned, in particular depending on the nature and the body weight of the subject to be treated, on individual behaviour to the medicament, the nature and severity of the disorder, the manner of preparation and administration, and the point or interval at which administration takes place.

STARTING COMPOUNDS

EXAMPLE I

3-Pyridylpropionyl chloride hydrochloride

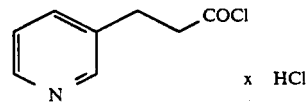

10.1 g (66.8 mmol) of 3-pyridylpropionic acid [cf. F. A. Walker and M. Benson, J. Am. Chem. Soc. 102, 5530 (1980)] are suspended in 30 ml of dichloromethane p.a. and 10.83 g (91 mmol) of thionyl chloride are slowly added. The mixture is boiled under reflux for 24 h, cooled and the resultant precipitate is filtered off with suction. The solid is washed with cold dichloromethane and ether and freed from residual solvent in a high vacuum. Yield: 12.13 g (58.9 mmol)

M.p.: 159°–161° C.

EXAMPLE II 3-(Hydroxy-(3-nitrophenyl)-methyl)-pyridine

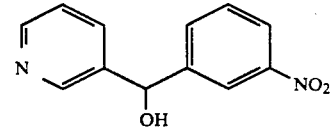

Analogously to the literature [R. N. Carde, P. C. Hayes, G. Jones and C. J. Cliff, J. Chem. Soc., Perkin Trans. I, 1981, 1132], 30.0 g (189.8 mmol) of 3-bromopyridine in 90 ml of absolute ether are slowly reacted at −70° C. with 64 ml of a 2.5 molar solution of n-butyllithium in ether, the mixture is subsequently stirred for 15 minutes after addition is complete and a solution of 29.0 g (192.0 mmol) of 3-nitrobenzaldehyde in 200 ml of abs. tetrahydrofuran is then added dropwise. The reaction mixture is subsequently stirred at −70° C. for 2 hours and at room temperature for 2 hours and is then stirred using water and 40% strength sodium hydrogen sulphate at 0° C. The aqueous phase is extracted several times using ether, and the organic phases are then dried using sodium sulphate and concentrated in a rotary evaporator. Column chromatography (silica gel 60, Merck, 40–63 μm, eluent: first toluene/ethyl acetate=1:1, later 1:4) yields 21.3 g (92.5 mmol) of product.

TLC (toluene:ethyl acetate=1:4)

R$_f$=0.22

EXAMPLE III 3-(3-Aminobenzyl)-pyridine

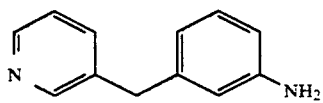

14.85 g (64.5 mmol) of the compound from Example II are hydrogenated with H₂ under normal pressure at room temperature on 7.4 g of palladium (10% strength on animal charcoal) in 500 ml of ethanol and 18 ml of concentrated hydrochloric acid. After 18 hours, the catalyst is filtered off, the solution is adjusted to pH 10 using aqueous 25% strength ammonia solution and the mixture obtained is concentrated to dryness in a rotary evaporator. The solid is thoroughly stirred with ethanol:ether =4:1 and filtered off, and the filtrate is evaporated.

Yield: 10.21 g (55.4 mmol) TLC (dichloromethane:-methanol=10:1)
$R_f$=0.61

EXAMPLE IV 3-(4-Hydrazinobenzyl)-pyridine

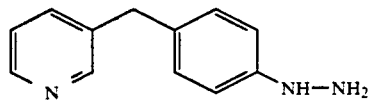

6.8 g (36.9 mmol) of 3-(4-aminobenzyl)-pyridine [EP 69,521] are dissolved in 9.2 ml of concentrated hydrochloric acid and 12 ml of water, and the solution is cooled to 5° C. and reacted with a solution of 2.55 g (36.9 mmol) of sodium nitrite in 17 ml of water. The reaction mixture is subsequently stirred at 0°-5° C. for 30 minutes, and then added dropwise at room temperature to 120 g of a 40% strength sodium hydrogen sulphite solution which has been adjusted to a pH of 6.5 using sodium hydroxide. The mixture is then boiled under reflux for 4 hours, the pH of 6.5 always being maintained. The mixture is cooled and poured into 120 ml of sodium hydroxide solution; the pH is then 12. After extraction using dichloromethane and drying using sodium sulphate, the mixture is concentrated in a rotary evaporator and 4.66 g (23.4 mmol) of product are obtained.

TLC: (toluene:acetone=2:1)
$R_f$=0.50

The compounds shown in Table 1 were obtained analogously to Example IV:

TABLE 1

| Ex. No. | R¹ | R² | $R_f$ |
|---|---|---|---|
| V | H | —CH₂—(4-pyridyl) | 0.39[a] |
| VI | —CH₂—(3-pyridyl) | H | 0.41[a] |
| VII | H | —CH₂—(3-pyridyl) | 0.50[a] |
| VIII | H | —(CH₂)₂—(3-pyridyl) | 0.46[b] |
| IX | (3-pyridyl) | H | 0.22[c] |

[a](toluene:acetone = 2:1)
[b](dichloromethane:methanol = 10:1)
[c](ethyl acetate:toluene = 4:1)

EXAMPLE X 9-(2-Cyano-ethyl)-6-hydroxy-3-(4-fluorophenylsulphonamido)-1,2,3,4-tetrahydrocarbazole

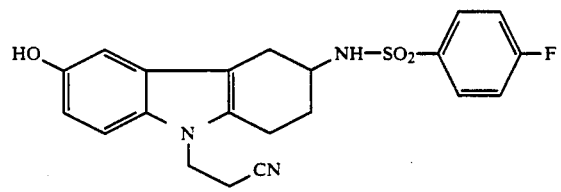

17.18 g (40.2 mmol) of 9-(2-cyano-ethyl)-3-(4-fluorophenylsulphonamide)-6-methoxy-1,2,3,4-tetrahydrocarbazole are dissolved under nitrogen in 200 ml of dichloromethane p.a. and reacted at −78° C. with 92.5 ml of a 1M solution of boron tribromide in dichloromethane. The mixture is stirred at −78° C. for 30 minutes, allowed to come to room temperature over the course of 30 minutes and subsequently stirred for 1 hour. After this, it is hydrolysed using 1.5 l of water and adjusted to a pH of 1 using 2N sulphuric acid. Extraction of the aqueous phase several times using ethyl acetate and drying of the organic phase using sodium sulphate yields a crude product, after evaporation of the solvent in a rotary evaporator, which is purified by column chromatography (silica gel 60, Merck, 40–63 μm, toluene:ethyl acetate=3:2).

TLC (toluene:ethyl acetate=3.2)
$R_f$=0.39

EXAMPLE XI (3R)-(4-Fluorophenylsulphonamido)-9-(2-methoxycarbonylethyl)-1,2,3,4-tetrahydrocarbazole

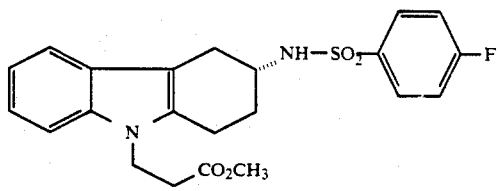

10.0 g (24 mmol) of (3R)-(4-fluorophenylsulphonamido)-9-(2-carboxy-ethyl)-1,2,3,4-tetrahydrocarbazole [cf. (German Offenlegungsschrift 3,631,824] are boiled under reflux for 2 hours with 5 ml of concentrated sulphuric acid in 100 ml of absolute methanol. After cooling, the mixture is neutralised using saturated sodium hydrogen carbonate solution, the alcohol content is evaporated in a rotary evaporator, and the mixture is made up to the original volume using water and extracted several times using dichloromethane. The organic phase is dried using sodium sulphate, evaporated and freed from residual solvent in a high vacuum.

Yield: 10.07 g (22.7 mmol)

TLC: $R_f$=0.52 (toluene:ethanol=6:1)

The analogous racemic 6-hydroxy derivative can correspondingly be obtained from the corresponding carboxylic acid:

TLC: $R_f$=0.59 (toluene:ethyl acetate=1:1)

EXAMPLE XII 3-(4-Fluorophenylsulphonamido)-6-methoxy-1,2,3,4-tetrahydrocarbazole

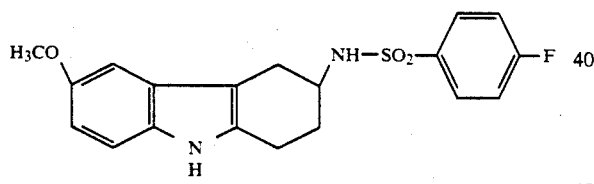

The title compound is prepared in analogy to the procedure of Example XVI which is shown later.

$R_f$=0.32 (toluene:ethyl acetate 4:1)

EXAMPLE XIII 9-(2-Cyanoethyl)-3-(4-fluorophenylsulphonamido)-6-methoxy-1,2,3,4-tetrahydrocarbazole

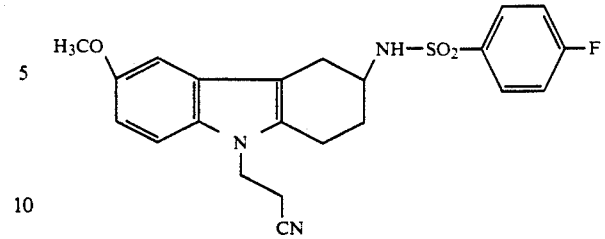

The title compound is prepared in analogy to the procedure of Example XXIV which is shown later.

$R_f$=0.22 (toluene:ethyl acetate 4:1)

EXAMPLE XIV 3-(4-Fluorophenylsulphonamido)-6-hydroxy-9-(2-carboxyethyl)-1,2,3,4-tetrahydrocarbazole

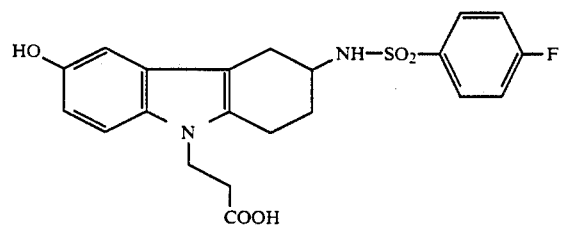

The title compound is prepared in analogy to the procedure of Example 11 which is described later.

$R_f$=0.59 (toluene:ethyl acetate 1:4)

EXAMPLE XV 3-(4-Chlorophenylsulphonamido)-6-fluoro-9-(2-(5-tetrazolyl)-ethyl)-1,2,3,4-tetrahydrocarbazole

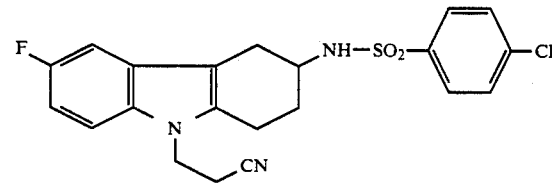

The title compound is prepared in analogy to the procedure of Example XXIV which is described later.

$R_f$=0.60 (dichloromethane:ethyl acetate=10:1)

EXAMPLE XVI 3-(4-Fluorophenylsulphonamido)-6-(3-pyridylmethyl)-1,2,3,4-tetrahydrocarbazole hydrochloride

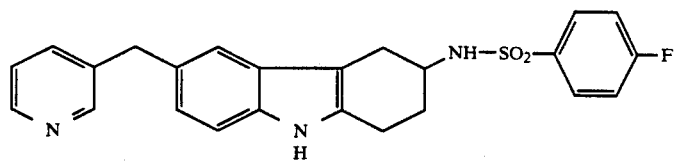

4.66 g (23.4 mmol) of the compound from Example IV are boiled under reflux for 8 hours with 6.25 g (23.4 mmol) of 4-(4-fluorophenylsulphonamido)-cyclohexanone [cf. DE 3,631,824] in 96 ml of ethanol and 5 ml of concentrated sulphuric acid. The mixture is then cooled, neutralised using sodium bicarbonate solution and extracted several times using ethyl acetate. The organic phase is dried using sodium sulphate, concentrated in a rotary evaporator and freed from residual solvent in a high vacuum. After column chromatography (silica gel 60, Merck 40-63 μm, ethyl acetate:-toluene=first 1:2, then 1:1, finally 2:1), 7.5 g of contaminated product are obtained, which is dissolved in dichloromethane and converted into its hydrochloride using hydrogen chloride gas. The mixture is concentrated in a rotary evaporator and the residue is thoroughly stirred with ether/petroleum ether (30°–50° C.). After filtering off with suction and drying in a high vacuum, 6.87 g (14.6 mmol) of product are obtained.

TLC (ethyl acetate:toluene=4:1)
$R_f$=0.55

The compounds shown in Table 2 can be prepared in analogy to Example XVI:

TABLE 2

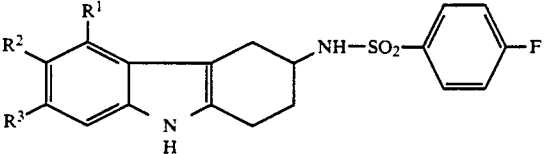

| Ex. No. | $R^1$ | $R^2$ | $R^3$ | $R_f$ |
|---------|-------|-------|-------|-------|
| XVII | H | 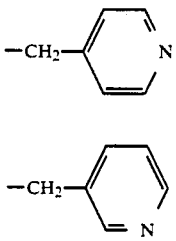 | H | 0.25[a] |
| XVIII | H | 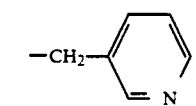 | H | 0.55[b] |
| XIX | H | H | 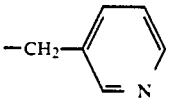 | 0.33[c] |
| XX | 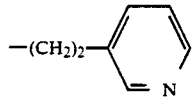 | H | H | 0.49[c] |
| XXI | H | 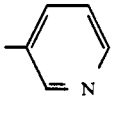 | H | 0.42[c] |
| XXII | 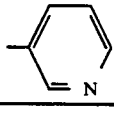 | H | H | 0.41[c] |
| XXIII | H | H |  | 0.24[c] |

Eluent mixtures:
[a] ethyl acetate:toluene = 1:1
[b] ethyl acetate:toluene = 4:1
[c] ethyl acetate:toluene = 2:1

EXAMPLE XXIV 9-(2-Cyanoethyl)-3-(4-fluorophenylsulphonamido)-6-(3-pyridylmethyl)-1,2,3,4-tetrahydro-carbazole

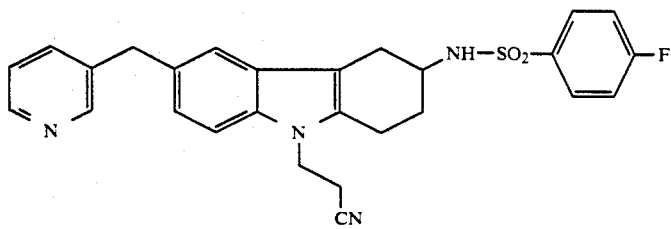

4.95 g (10.5 mmol) of the compound from Example XVI are dissolved in 100 ml of dimethylformamide p.a., deprotonated using 0.693 g (23.1 mmol) of sodium hydride (stabilised with 20% paraffin oil) and then reacted at room temperature with 1.5 ml (22.8 mmol) of acrylonitrile. The reaction is incomplete after 2 h, therefore 0.071 g (2.4 mmol) of sodium hydride and 0.7 ml (10.6 mmol) of acrylonitrile are added; the reaction has progressed to completion after 1 hour. Water is added and the mixture is extracted using ethyl acetate; insoluble constituents can be removed by filtering off with suction through kieselguhr/silica gel. The organic phase is washed with water, dried using sodium sulphate and evaporated. The crude product is purified by column chromatography (silica gel 60, Merck, 40-63 μm, ethyl acetate:toluene=4:1).

Yield: 4.97 g (10.2 mmol)
TLC (ethyl acetate:toluene=4:1)
$R_f$=0.46

The compounds shown in Table 3 were prepared analogously to Example XXIV:

TABLE 3

| Ex. No. | R¹ | R² | R³ | $R_f$ |
|---|---|---|---|---|
| XXV | H | —CH₂-(4-pyridyl) | H | 0.36[a] |
| XXVI | H | —CH₂-(3-pyridyl) | H | 0.46[a] |
| XXVII | H | H | —CH₂-(3-pyridyl) | 0.27[a] |
| XXVIII | H | —(CH₂)₂-(3-pyridyl) | H | 0.40[a] |
| XXIX | H | —CH₂-(3-pyridyl) | H | 0.34[b] |
| XXX | (3-pyridyl) | H | H | 0.48[a] |

TABLE 3-continued

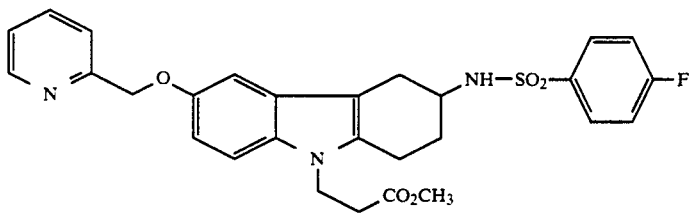

| Ex. No. | R¹ | R² | R³ | $R_f$ |
|---|---|---|---|---|
| XXXI | H | H | (3-pyridyl) | 0.24[a] |

[a] ethyl acetate:toluene = 4:1
[b] ethyl acetate:toluene = 2:1

PREPARATION EXAMPLES (compounds of the general formula I)

EXAMPLE 1

3-(4-Chlorophenylsulphonamido)-6-fluoro-9-(2-(5-tetrazolyl)-ethyl)-1,2,3,4-tetrahydrocarbazole

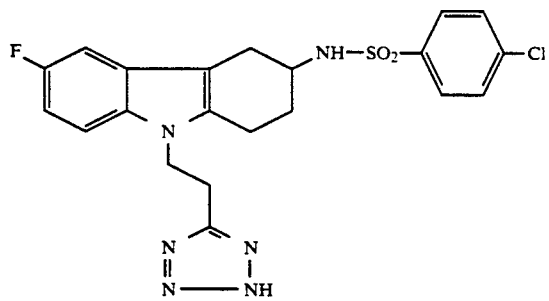

2.9 g (6.7 mmol) of the compound from Example XV are reacted under reflux for 17 hours under protective gas with 2.18 g (33.6 mmol) of sodium azide and 4.62 g (33.6 mmol) of triethylammonium chloride in 30 ml of abs. dimethylformamide. The mixture is diluted with 1M sulphuric acid and ethyl acetate, the phases are separated and the organic phase is washed several times with sulphuric acid. After drying using sodium sulphate, the solvent is evaporated and the residue is purified by chromatography (silica gel 60, Merck, 40–63 μm, dichloromethane:methanol = 10:1).

Yield: 2.1 g (4.4 mmol)
$R_f$ = 0.13 (dichloromethane:methanol = 10:1)

EXAMPLE 2

3-(4-Fluorophenylsulphonamido)-9-(2-methoxycarbonylethyl)-6-(2-pyridyl-methoxy)-1,2,3,4-tetrahydrocarbazole 1.5 g (3.34 mmol) of 3-(4-fluorophenylsulphonamido)-6-hydroxy-9-(2-methoxycarbonyl-ethyl)-1,2,3,4-tetrahydrocarbazole are dissolved in 30 ml of dimethylformamide p.a. at room temperature under nitrogen and the solution is reacted with 303 mg (10.08 mmol) of sodium hydride (80% strength, stabilised with paraffin oil). After evolution of hydrogen is complete, 0.55 g (3.34 mmol) of 2-chloromethylpyridine hydrochloride is added and the mixture is stirred at 60° C. for 1 hour. Water is added to the reaction mixture obtained and the mixture is extracted several times using ethyl acetate. The organic extracts are dried using sodium sulphate and evaporated. To separate the products, the residue is chromatographed on silica gel 60 (Merck, 40–63 μm, toluene:ethyl acetate = 4:1 to 2:1).

Yields: 120 mg (0.22 mmol) of title product of
$R_f$ = 0.41 (toluene:ethyl acetate 1:1)
97 mg (0.18 mmol) of 6-hydroxy-9-(2-methoxycarbonyl-ethyl)- 3-(N-(2-pyridylmethyl)-N-(4-fluorophenyl)-sulphonamido-1,2,3,4-tetrahydrocarbazole of $R_f$ = 0.35 (toluene:ethyl acetate 1:1)
189 mg (0.30 mmol) of 9-(2-methoxycarbonylethyl)-6-(2-pyridyl-methoxy)-3-(N-(2-pyridylmethyl)-N-(4-fluorophenyl)sulphonamido)-1,2,3,4-tetrahydrocarbazole of $R_f$ = 0.20 (toluene:ethyl acetate 1:1).

The compounds shown in Table 4 were prepared analogously to the procedure of Example 2:

TABLE 4

(2-(3-pyridyl)ethyl-carbonyl)-1,2,3,4-tetrahydrocarbazole (8)

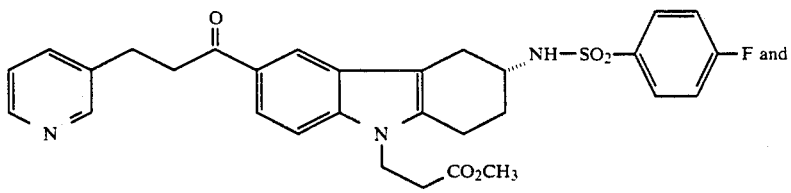
(7)

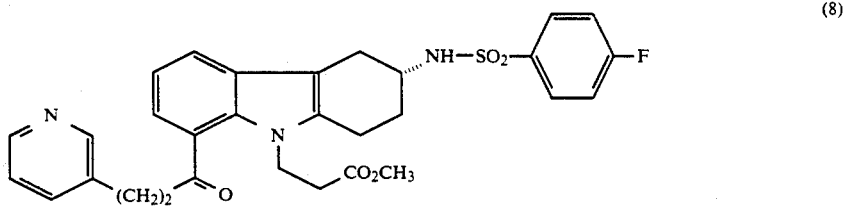
(8)

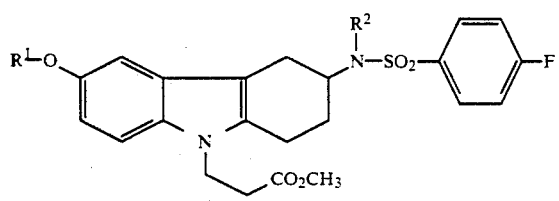

| Ex. No. | R¹ | R² | R$_f$* |
|---|---|---|---|
| 3 | —CH$_2$—(4-pyridyl) | H | 0.24 |
| 4 | H | —CH$_2$—(4-pyridyl) | 0.13 |
| 5 | —CH$_2$—(3-pyridyl) | H | 0.26 |
| 6 | H | —CH$_2$—(3-pyridyl) | 0.15 |

*toluene:ethyl acetate = 1:1

EXAMPLE 7 AND EXAMPLE 8

(3R)-(4-fluorophenylsulphonamido)-9-(2-methoxycarbonylethyl)-6-(2-(3-pyridyl)ethyl-carbonyl)-1,2,3,4-tetrahydrocarbazole (7) and (3R)-(4-fluorophenylsulphonamido)-9-(2-methoxycarbonyl-ethyl)-8-(2-(3-pyridyl)ethyl-carbonyl)-1,2,3,4-tetrahydrocarbazole (8)

3.10 g (7.2 mmol) of the compound from Example XI are dissolved in 60 ml of 1,2-dichloroethane p.a., 2.23 g (10.8 mmol) of 3-pyridylpropionyl chloride hydrochloride and 1.92 g (14.2 mmol) of aluminium chloride (anhydrous) are added and the mixture is boiled under reflux for 2 days. The cooled reaction mixture is poured into 100 ml of saturated aqueous sodium hydrogen carbonate solution and the mixture is extracted several times using dichloromethane; the organic phase is dried using sodium sulphate and concentrated. To separate the isomers, the residue is chromatographed on silica gel 60 (Merck, 40–63 μm, toluene:ethyl acetate=2:1).

Yield: of (22) 0.52 g (0.9 mmol) and of (23) 0.41 g (0.7 mmol); the mixed fraction obtained can be separated further.

TLC (toluene:ethyl acetate=1:1)
R$_f$=0.16 (22)
R$_f$=0.12 (23)

EXAMPLE 9

(3R)-(4-fluorophenylsulphonoamido)-9-(2-methoxycarbonylethyl)-6-(3-(3-pyridyl)-propyl)-1,2,3,4-tetrahydrocarbazole

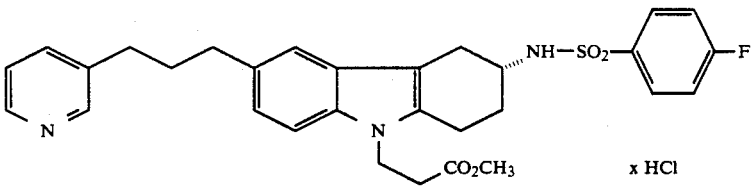
x HCl 260 mg (0.46 mmol) of the compound from Example (7) are reacted with 17.4 mg (0.46 mmol) of sodium borohydride in 25 ml of abs. tetrahydrofuran at room temperature. If starting material is still present after 4 hours, a further 17.4 mg (0.46 mmol) of sodium borohydride is added and the mixture is stirred overnight. 30 ml of 0.1M hydrochloric acid is added to this mixture and it is extracted several times using 25 ml of ethyl acetate each time. The organic phases dried using sodium sulphate are evaporated and the crude product obtained is purified by chromatography (silica gel 60, Merck, 40–63 μm, toluene:ethyl acetate=4:1 to 2:1).

Yield: 127 mg (0.23 mmol)
TLC (toluene:ethyl acetate=1:4) R$_f$=0.66

EXAMPLE 10

(3R)-((4-fluorophenylsulphonamido)-9-(2-methoxycarbonylethyl)-8-(3-(3-pyridyl)-propyl-1,2,3,4-tetrahydrocarbazole

EXAMPLE 11

9-(2-Carboxyethyl)-3-(4-fluorophenylsulphonamido)-6-(3-pyridyl-methyl)-1,2,3,4-tetrahydro-carbazole hydrochloride

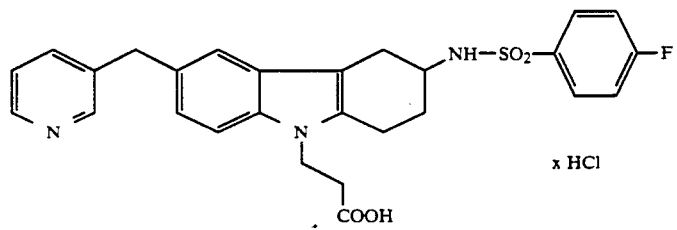

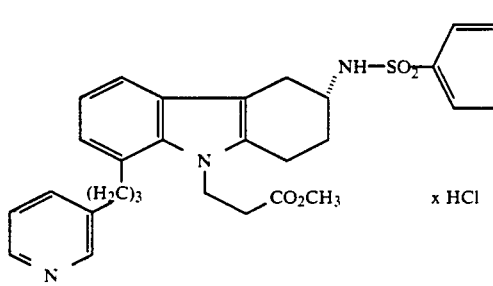

The title compound is prepared in analogy to the procedure of Example 9.

TLC: $R_f$=0.59 (toluene:ethyl acetate=1:4)

4.74 g (9.7 mmol) of the compound from Example XXVI are dissolved in 20 ml of ethanol, 17 ml of 2M NaOH and 20 ml of water are added and the mixture is boiled under reflux for 2 hours. The cooled reaction mixture is extracted once using dichloromethane and once using ether, the aqueous phase is adjusted to pH 5 using 2M hydrochloric acid, and the resultant precipitate is filtered off with suction and washed with water. The product is dried over $P_4O_{10}$ in vacuo.

Yield: 5.03 g (9.2 mmol)

TLC ($CH_2Cl_2:CH_3OH$=10:1) $R_f$=0.30

The compounds shown in Tables 5 and 6 can be prepared in analogy to the procedure of Example 11.

TABLE 5

| Ex. No. | $R^1$ | $R^2$ | $R^3$ | $R^4$ | $R_f$ |
|---|---|---|---|---|---|
| 12 | H | —O—CH₂—(3-pyridyl) | H | H | 0.25 |
| 13 | H | —O—CH₂—(4-pyridyl) | H | H | 0.16 |
| 14 | H | —O—CH₂—(2-pyridyl) | H | H | 0.35 |
| 15 | H | —CH₂—(4-pyridyl) | H | H | 0.12 |
| 16 | H | H | —CH₂—(3-pyridyl) | H | 0.27 |

TABLE 5-continued
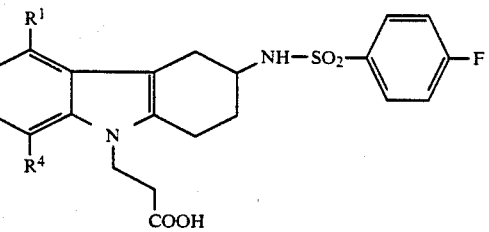
| Ex. No. | R¹ | R² | R³ | R⁴ | $R_f$ |
|---|---|---|---|---|---|
| 17 | H | —(CH₂)₂—(3-pyridyl) | H | H | 0.31 |
| 18 | —CH₂—(3-pyridyl) | H | H | H | 0.35 |
| 19 | H | H | H | —CO—(CH₂)₂—(3-pyridyl) | 0.05 |
| 20 | H | —CO—(CH₂)₂—(3-pyridyl) | H | H | 0.05 |
| 21 | H | —(CH₂)₃—(3-pyridyl) | H | H | 0.17 |
| 22 | H | H | H | —(CH₂)₃—(3-pyridyl) | 0.10 |
| 23 | (3-pyridyl) | H | H | H | 0.29 |
| 24 | H | H | (3-pyridyl) | H | 0.19 |
*Eluent = CH₂Cl₂:CH₃OH = 10:1

TABLE 6

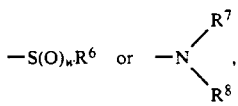

| Ex. No. | R¹ | R² | $R_f$* |
|---|---|---|---|
| 25 | -CH₂-(2-pyridyl) | -CH₂-(2-pyridyl) | 0.50 |
| 26 | H | -CH₂-(4-pyridyl) | 0.24 |

*Eluent = dichloromethane:methanol 10:1

What is claimed is:

1. A heterocyclically substituted cycloalkano(b)indolesulphonamide of the formula

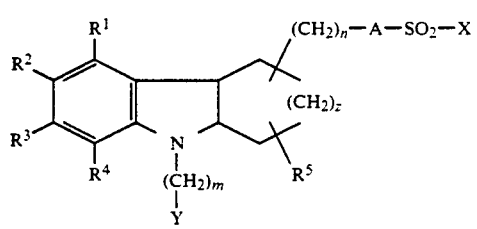

in which
R$^1$, R$^2$, R$^3$, R$^4$ and R$^5$ are identical or different and
represent hydrogen, nitro, cyano, halogen, trifluoromethyl, carboxyl, hydroxyl or trifluoromethoxy, or
represent a group of the formula —S(O)$_w$R$^6$,
in which
R$^6$—denotes straight-chain or branched alkyl having up to 8 carbon atoms or aryl having 6 to 10 carbon atoms, which, for its part, is substituted by halogen, nitro, cyano or trifluoromethyl
and
w—denotes a number 0, 1 or 2,
or
represent straight-chain or branched alkoxy or alkoxycarbonyl in each case having up to 10 carbon atoms or benzyloxy, or
represent a group of the formula —NR$^7$R$^8$, in which
R$^7$ and R$^8$ are identical or different and
denote hydrogen, straight-chain or branched alkyl or acyl in each case having up to 8 carbon atoms or
denote aryl having 6 to 10 carbon atoms,
or
R$^1$, R$^2$, R$^3$, R$^4$ and R$^5$ are identical or different and,
represent cycloalkyl having 3 to 8 carbon atoms or
represent aryl having 6 to 10 carbon atoms, or
represent straight-chain or branched alkyl or alkenyl in each case having up to 10 carbon atoms, which are optionally substituted by halogen, hydroxyl, carboxyl, cyano, aryl having 6 to 10 carbon atoms, straight-chain or branched alkyl, alkoxy or alkoxycarbonyl in each case having up to 8 carbon atoms or by a group of the formula $$-S(O)_wR^6 \quad \text{or} \quad -N\begin{matrix}R^7\\R^8\end{matrix},$$

in which
w, R$^6$, R$^7$ and R$^8$ have the abovementioned meaning, or
only one of R$^1$, R$^2$, R$^3$, R$^4$ or R$^5$
represents a group of the formula —D, —E—O—L—D, —E—NH—L—D,
—E—CO—L—D or —E—D, in which
D—denotes thienyl, furyl, pyrrolyl, pyrazolyl, pyridyl, pyrimidyl, pyrazinyl, pyridazinyl, quinolyl, isoquinolyl, quinazolyl, quinoxazolyl, tetrazolyl, cinnolyl, thiazolyl, benzothiazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl, or piperazinyl,
and
E and L are identical or different and
denote a direct bond or
denote straight-chain or branched alkylene or alkenylene having up to 10 carbon atoms,
X—represents aryl having to 6 to 10 carbon atoms, which is optionally monosubstituted to pentasubstituted by identical or different substituents from the group consisting of nitro, halogen, cyano, trifluoromethyl, trifluoromethoxy, trifluoromethylthio, hydroxyl, carboxyl, aryl or aryloxy having 6 to 10 carbon atoms and straight-chain or branched alkoxy or alkoxycarbonyl in each case having up to 8 carbon atoms or by straight-chain or branched alkyl having up to 8 carbon atoms, it being possible for the alkyl, for its part, to be substituted by carboxyl, hydroxyl, alkoxycarbonyl having up to 6 carbon atoms, by aryl having 6 to 10 carbon atoms, or
by a group of the formula —S(O)$_w$R$^6$ or —NR$^7$R$^8$,
in which
w, R$^6$, R$^7$ and R$^8$ have the abovementioned meaning,
or
X—represents straight-chain or branched alkyl having up to 8 carbon atoms or represents trifluoromethyl,
m—represents the number 1, 2, 3 or 4,
n—represents the number 0, 1 or 2,
z—represents a number 1, 2, 3 or 4,
A—represents a direct bond or a group of the formula —NH— or —N—E—D, in which D and E have the abovementioned meaning,
Y—represents the group of the formula —CO—G, in which
G—denotes hydroxyl, alkoxy having up to 8 carbon atoms, phenoxy or a group of the formula —NR$^7$R$^8$ or —NH—SO$_2$—R$^6$, in which $R^6$, $R^7$ and $R^8$ have the abovementioned meaning, or represents tetrazolyl, with the proviso that if A represents a direct bond or a group of the formula

one of the substituents $R^1$, $R^2$, $R^3$, $R^4$ and $R^5$ must represent one of the groups —D, —E—O—L—D, —E—N-H—L—D, —E—CO—L—D or —E—D, if appropriate in an isomeric form, or a salt thereof.

2. A heterocyclically substituted cycloalkano(b)indolesulphonamide isomers or salts thereof according to claim 1, in which $R^1$, $R^2$, $R^3$, $R^4$ and $R^5$ are identical or different and represent hydrogen, fluorine, chlorine, bromine, nitro, cyano, trifluoromethyl, carboxyl, hydroxyl or trifluoromethoxy, represent a group of the formula —S(O)$_w$R$^6$, in which $R^6$—denotes straight-chain or branched alkyl having up to 6 carbon atoms or phenyl, which, for its part, can be substituted by fluorine, chlorine, bromine, nitro, cyano or trifluoromethyl, w—denotes a number 0, 1 or 2, or represent straight-chain or branched alkoxy or alkoxycarbonyl in each case having up to 8 carbon atoms, or represent a group of the formula —NR$^7$R$^8$, in which $R^7$ and $R^8$ are identical or different and denote hydrogen, straight-chain or branched alkyl having up to 8 carbon atoms or phenyl, or represent cyclopropyl, cyclopentyl, cyclohexyl or phenyl, or represent straight-chain or branched alkyl or alkenyl in each case having up to 8 carbon atoms, which are optionally substituted by fluorine, chlorine, bromine, hydroxyl, carboxyl, cyano, phenyl, straight-chain or branched alkyl, alkoxy or alkoxycarbonyl in each case having up to 6 carbon atoms or by group of the formula

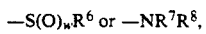

in which w, $R^6$, $R^7$ and $R^8$ have the abovementioned meaning, or only one of $R^1$, $R^2$, $R^3$, $R^4$ or $R^5$ represents a radical or a group of the formula —D, —E—O—L—D, —E—NH—L—D, —E—CO—L—D or —E—D in which D—denotes pyridyl, quinolyl, tetrazolyl, benzothiazolyl, isoquinolyl, benzimidazolyl, pyrimidyl, pyrrolyl, thienyl, furyl, imidazolyl or thiazolyl, and E and L are identical or different and denote a direct bond or denote straight-chain or branched alkyl or alkenyl in each case having up to 8 carbon atoms, X—represents phenyl which is optionally monosubstituted to tetrasubstituted by identical or different substituents from the series comprising nitro, hydroxyl, fluorine, chlorine, bromine, iodine, cyano, trifluoromethyl, trifluoromethoxy, hydroxyl, carboxyl, phenyl, phenoxy and straight-chain or branched alkoxy or alkoxycarbonyl in each case having up to 6 carbon atoms or by straight-chain or branched alkyl having up to 6 carbhon atoms, or represents straight-chain or branched alkyl having up to 6 carbon atoms or trifluoromethyl, m—represents the number 1, 2 or 3, n—represents the number 0 or 1, z—represents a number 1, 2 or 3, A—represents a direct bond or a group of the formula

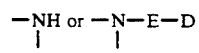

in which D and E have the abovementioned meaning,

Y—represents the group of the formula —CO—G, in which

G—denotes hydroxyl, alkoxy having up to 6 carbon atoms, phenoxy or the group —NHSO$_2$R$^6$, in which $R^6$ has the abovementioned meaning, or represents tetrazolyl, with the proviso that if A represents a direct bond or a group of the formula —NH—, one of the substituents $R^1$, $R^2$, $R^3$, $R^4$ and $R^5$ must represent one of the groups —D, —E—O—L—D, —E—NH—L—D, —E—CO—L—D or —E—D.

3. A heterocyclically substituted cycloalkano(b)indolesulphonamide isomers or salts thereof according to claim 1, in which R1, R2, R3, R4 and R5 are identical or different and represent hydrogen, fluorine or chlorine, represent a group of the formula —S(O)$_w$R$^6$, in which $R^6$—denotes straight-chain or branched alkyl having up to 4 carbon atoms or phenyl, which, for its part, can be substituted by fluorine, chlorine, bromine, w—denotes the number 2, or represent straight-chain or branched alkoxy or alkoxycarbonyl in each case having up to 4 carbon atoms, or represent a group of the formula —NR$^7$R$^8$, in which $R^7$ and $R^8$ are identical or different and denote hydrogen, straight-chain or branched alkyl having up to 4 carbon atoms or phenyl, or represent straight-chain or branched alkyl having up to 6 carbon atoms, which are optionally substituted by fluorine, chlorine, bromine, hydroxyl, cyano or phenyl, or represent a radical or a group of the formula

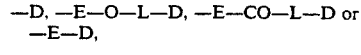

in which

D—denotes pyridyl, pyrimidyl, imidazolyl or thiazolyl, and

E and L are identical or different and
  denote a direct bond or
    denote straight-chain or branched alkyl having up to 6 carbon atoms,
X—represents phenyl which is optionally monosubstituted to tetrasubstituted by identical or different substituents from the group consisting of fluorine, chlorine, bromine, cyano, trifluoromethyl and trifluoromethoxy or by straight-chain or branched alkyl, alkoxy or alkoxycarbonyl in each case having up to 4 carbon atoms,
m—represents the number 1 or 2,
n—represents the number 0 or 1,
z—represents a number 1 or 2,
A—represents a direct bond or a group of the formula —NH or —N—E—D in which
  D and E have the abovementioned meaning,
Y—represents the group of the formula —CO—G, in which
  G—denotes hydroxyl, alkoxy having up to 4 carbon atoms or the group —NHSO$_2$R$^6$,
    in which
      R$^6$ has the abovementioned meaning.
or
  represents tetrazolyl,
with the proviso that if A represents a direct bond or a group of the formula —NH—, at least one of the substituents R$^1$, R$^2$, R$^3$, R$^4$ and R$^5$ must represent one of the groups —D, —E—O—L—D, —E—NH—L—D, —E—CO—L—D or —E—D if appropriate in an isomeric form, and their salts.

4. A compound according to claim 1, wherein such compound is 9-(2-carboxyethyl)-3-(4-fluorophenylsulphonamido)-6-(3-pyridyl-methyl)-1,2,3,4-tetrahydrocarbazol of the formula

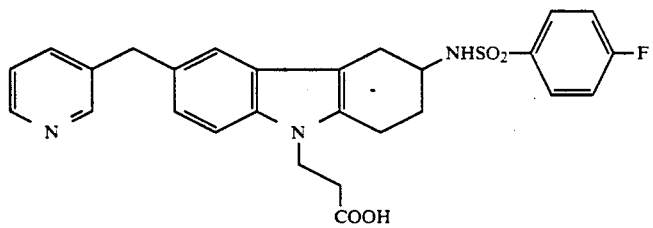

or a salt thereof.

5. A compound according to claim 1, wherein such compound is 9-(2-carboxyethyl)-3-(4-fluorophenylsulphonamido)-7-(3-pyridyl-methyl)-1,2,3,4-tetrahydrocarbazol of the formula

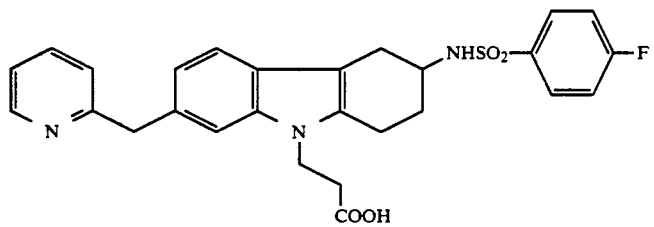

or a salt thereof.

6. A compound according to claim 1, wherein such compound is 9-(2-carboxyethyl)-3-(4-fluorophenylsulphonamido)-5-(3-pyridyl-methyl)-1,2,3,4-tetrahydrocarbazol of the formula

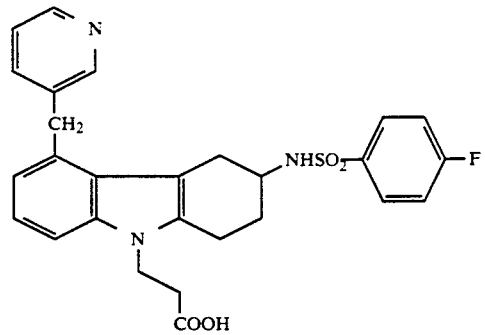

or a salt thereof.

7. A compound according to claim 1, wherein such compound is 9-(2-carboxyethyl)-3-(4-fluorophenylsulphonamido)-7-(3-pyridyl)-1,2,3,4-tetrahydrocarbazol of the formula

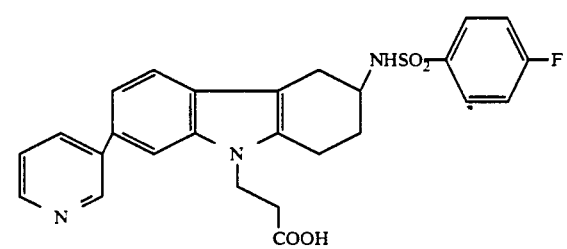

or a salt thereof.

8. A composition for the treatment of thromboembolic disorders comprising an amount effective therefor of a compound or a salt thereof according to claim 1 a carrier and a pharmaceutically acceptable diluent.

9. A method of treating thromboembolic disorders in a patient in need thereof which comprises administering to such patient an amount effective therefor of a compound or a salt thereof according to claim 1.

10. A method of treating thromboembolic disorders in a patient in need thereof which comprises administering to such patient an amount effective therefor of a compound or a salt thereof according to claim 1, wherein such compound is 9-(2-carboxyethyl)-3-(4-fluorophenylsulphonamido)-6-(3-pyridyl-methyl)-1,2,3,4-tetrahydro-carbazol, 9-(2-carboxyethyl)-3-(4-fluorophenyl-sulphonamido)-7-(3-pyridyl-methyl)-1,2,3,4-tetrahydro-carbazol, 9-(2-carboxyethyl)-3-(4-fluorophenyl-sulphonamido)-5-(3-pyridyl-methyl)-1,2,3,4-tetrahydro-carbazol, and 9-(2-carboxyethyl)-3-(4-fluorophenyl-sulphonamido)-7-(3-pyridyl)-1,2,3,4-tetrahydro-carbazol.

* * * * *